United States Patent
Goldsmith et al.

(10) Patent No.: US 6,372,956 B1
(45) Date of Patent: Apr. 16, 2002

(54) TRANSGENIC RATS AND RAT CELL LINES EXPRESSING HUMAN CD4 AND A HUMAN CHEMOKINE RECEPTOR

(75) Inventors: Mark A. Goldsmith, San Francisco, CA (US); Roberto F. Speck, Zurich (CH); Robert E. Atchison; Oliver Keppler, both of San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 0 days.

(21) Appl. No.: 09/470,817

(22) Filed: Dec. 23, 1999

Related U.S. Application Data

(60) Provisional application No. 60/114,443, filed on Dec. 31, 1998.

(51) Int. Cl.[7] .................. A01K 67/027; G01N 33/00; C12N 5/06
(52) U.S. Cl. ............... 800/14; 800/3; 435/353
(58) Field of Search ................ 800/3, 11, 18, 800/14, 8, 9; 424/130.1; 435/353

(56) References Cited

U.S. PATENT DOCUMENTS 5,656,271 A * 8/1997 MacDonald et al. ..... 424/131.1

OTHER PUBLICATIONS

Browning et al (1997) Proced. Nat. Acad. Sci. 94, 14637–14641.*
Houdebine (1994) J. Biotech. 34, 269–287.*
Mullins et al (1996) J. Clinc. Invest. 98, S37–S40.*
Wall (1996) Theriogenology 45, 57–68.*
Browning et al. (Dec. 1997), "Mice Transgenic for Human CD4 and CCR5 are Susceptible to HIV Infection," *Proc. Natl. Acad. Sci USA*, vol. 94:14637–14641.
Speck et al. (Jul. 1998), "Rabbit Cells Expressing Human CD4 and CCR5 are Highly Permissive for Human Immunodeficiency Virus Type 1 Infection," *Journal of Virology*, vol. 72(7):57285734.

* cited by examiner

*Primary Examiner*—Deborah Crouch
(74) *Attorney, Agent, or Firm*—Kathleen S. Hall; Bozicevic, Field & Francis, LLP

(57) ABSTRACT

The present invention features transgenic rodent models for HIV, wherein the transgenic rodent or transgenic rodent cell has incorporated into its genome genes encoding a human CD4 receptor and a human chemokine receptor. In particular the invention relates to transgenic rats, or mice characterized by being susceptible to infection with HIV, capable of expressing HIV structural genes, or HIV replication. The transgenic rodent or rodent cell of this invention is useful for studying the molecular basis of HIV infection, replication and pathogenicity, as well as for the testing of agents for new antiviral or vaccine strategies.

21 Claims, 7 Drawing Sheets

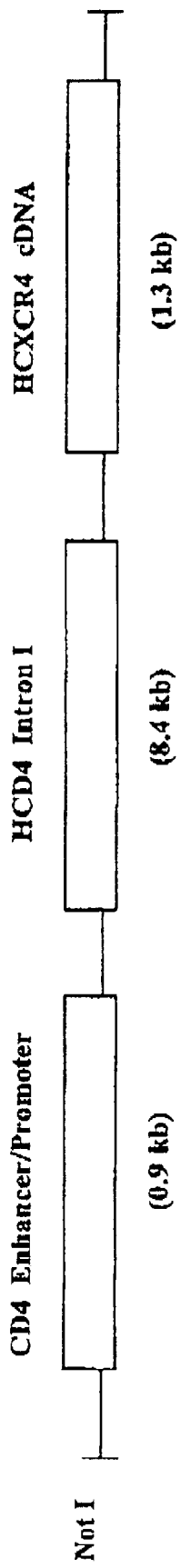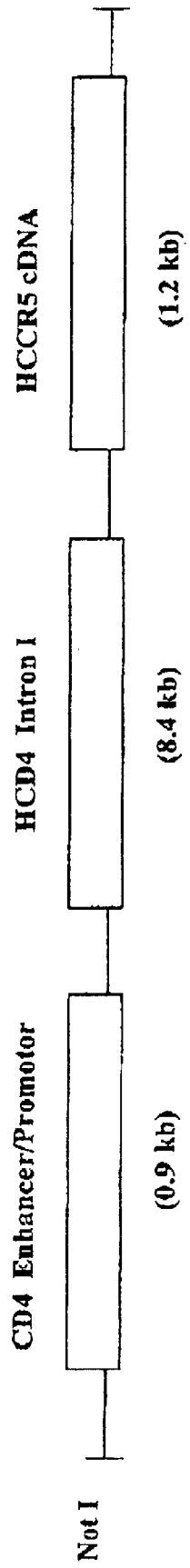

TRANSGENIC RATS AND RAT CELL LINES EXPRESSING HUMAN CD4 AND A HUMAN CHEMOKINE RECEPTOR

This appln claims benefit of Prov. No. 60/114,443 filed Dec. 31, 1998.

GOVERNMENT RIGHTS

The United States Government may have certain rights in this application pursuant to NIH Grant No. R21 AI42654-02.

FIELD OF THE INVENTION

The invention relates generally to the field of non-human, transgenic animal models for human immunodeficiency virus (HIV), and more specifically to the production and methods of use of a rodent model for HIV.

BACKGROUND OF THE INVENTION

Acquired Immune Deficiency Syndrome (AIDS) is a severe immunodeficiency disorder caused by infection with the human immunodeficiency virus (HIV). It is recognized that a major consequence of infection with HIV is the substantial loss of a class of T-cells commonly known as "helper" T-cells, which are the target cells for HIV infection. The entry of HIV into these and other target cells requires the interaction of the HIV virus with cell-surface CD4 molecules and a chemokine receptor, with different strains of HIV exhibiting both cellular and chemokine receptor specificity. (Speck et al., (1997) *J. of Virol* 71(9):7136–7139). Amino acids in the HIV env protein appear to determine the cellular tropism of an HIV strain as well as chemokine receptor preference (Speck et al., supra). For example, the chemokine receptor CCR5 mediates entry of HIV by macrophage-tropic strains (Deng, et al., *Nature* 381:661–666 (1996), whereas the chemokine receptor CXCR4 mediates viral entry for T cell line-tropic isolates (Feng, et al., *Science* 272:872–877 (1996)).

Transgenic rabbits expressing human CD4 have been generated in an effort to develop transgenic rabbit models of HIV disease.(Dunn, C. S., et al., *J. Gen. Virol.* 76 (Pt 6):1327–1336 (1995); Gillespie, F. P., et al., *Mol. Cell Biol.* 13:2952–2958 (1993); Leno, M. et al., *Virology* 213:450–454 (1995); U.S. Pat. No. 5,529,765). These studies demonstrated that transgenic rabbits expressing human CD4 were more susceptible to infection by HIV-1 than were their normal, non-transgenic counterparts. However, similar studies with transgenic mice expressing human CD4 showed that mouse cells are resistant to infection with HIV (Lores et al., (1992) *AIDS Res. Hum. Retroviruses* 8;2063). The reason for this difference in infectivity between the human CD4 transgenic rabbit model and the human CD4 transgenic mouse appears to be related to species-specific cofactors for post-entry viral processes.

Thus, there is a need for animal models within the HIV field that provide a more efficient, and cost-effective method of studying HIV infection in vivo. Rodent models are a more desirable model for HIV due to many characteristics such as size, reproductive cycle, cost of care, and the like. There is also a need in the HIV field for an animal model with a well characterized immune system.

SUMMARY OF THE INVENTION

The present invention features transgenic rodent animal models (e.g. rats, mice, and hamsters) for the study of HIV infection and replication, wherein the transgenic rodent is characterized by 1) expression of a human CD4 receptor and 2) expression of one or more human chemokine receptors. The transgenic animals may be either homozygous or heterozygous for these alterations. The bigenic or polygenic animals of the invention are further characterized by enhanced HIV infectivity and HIV replication within the cells of the transgenic rodent, both in vivo and in an in vitro culture of cells from these animals.

It is a general object of this invention to provide a transgenic rodent, in particular rodents belonging to a genus selected from Mus (e.g.—mice), Rattus (e.g.—Rat), and Mesocricetus (e.g.—hamsters), having stably integrated into its genome a human CD4 receptor and/or a human chemokine receptor, which transgenic rodent is susceptible to HIV infection.

In one aspect the invention features a method of screening for biologically active agents that modulate phenomena associated with HIV infection (e.g. immunosuppression, associated opportunistic infections, cancerous growths, etc), wherein the method involves the steps of combining a candidate agent with a transgenic rodent having 1) expression of a human CD4 receptor and 2) expression of a human chemokine receptor, and determining the effect of said agent upon a phenomenon associated with HIV infection. For example, the invention provides a method for using the animals of the invention in a screen for a vaccine that disrupts viral processes.

A primary object of this invention is to provide a transgenic rodent model for examining the effects of a candidate agent (e.g. a small molecule drug, endogenous factor, antiviral agent, etc.) on a phenomenon associated with HIV infection. Such transgenic animal models are useful for screening candidate agents for use in preventing, treating or relieving the symptoms of ARC and/or AIDS.

Another object is to provide a rodent model for HIV infection, thereby providing a useful means to study progression of infectivity and the associated syndromes, and in identifying means for preventing HIV infection.

It is yet another object of this invention to provide a transgenic rodent or transgenic rodent cell expressing the structural genes of HIV.

Yet another object is to provide a model for the assessment of infectivity and pathogenicity of a particular isolate of HIV.

In another aspect of the invention, the transgenic rodents of the invention are further manipulated to allow expression of a human gene that binds to a viral sequence, for example a gene encoding a protein that interacts with an HIV transactivation domain such as Tat. Preferably, this human gene is Cyclin T.

A feature of the invention is that transgenic rodents (e.g. mice and rats) of the invention have cells which express human CD4 receptor and a human chemokine receptor on their surface.

An advantage of the invention is that transgenic rodents or rodent cells (e.g. rats and mice) of the invention are infected and support viral replication upon inoculation with a variety of different strains of HIV.

These and other objects, advantages and features of the present invention will become apparent to those persons skilled in the art upon reading the details of the invention more fully set forth below.

BRIEF DESCRIPTION OF THE DRAWINGS

FIGS. 2–5 are schematic representations of transgenic vectors used to prepare transgenic rat lines carrying human CD4, CCR5, and CXCR4.

DETAILED DESCRIPTION OF THE INVENTION

Figure 1:
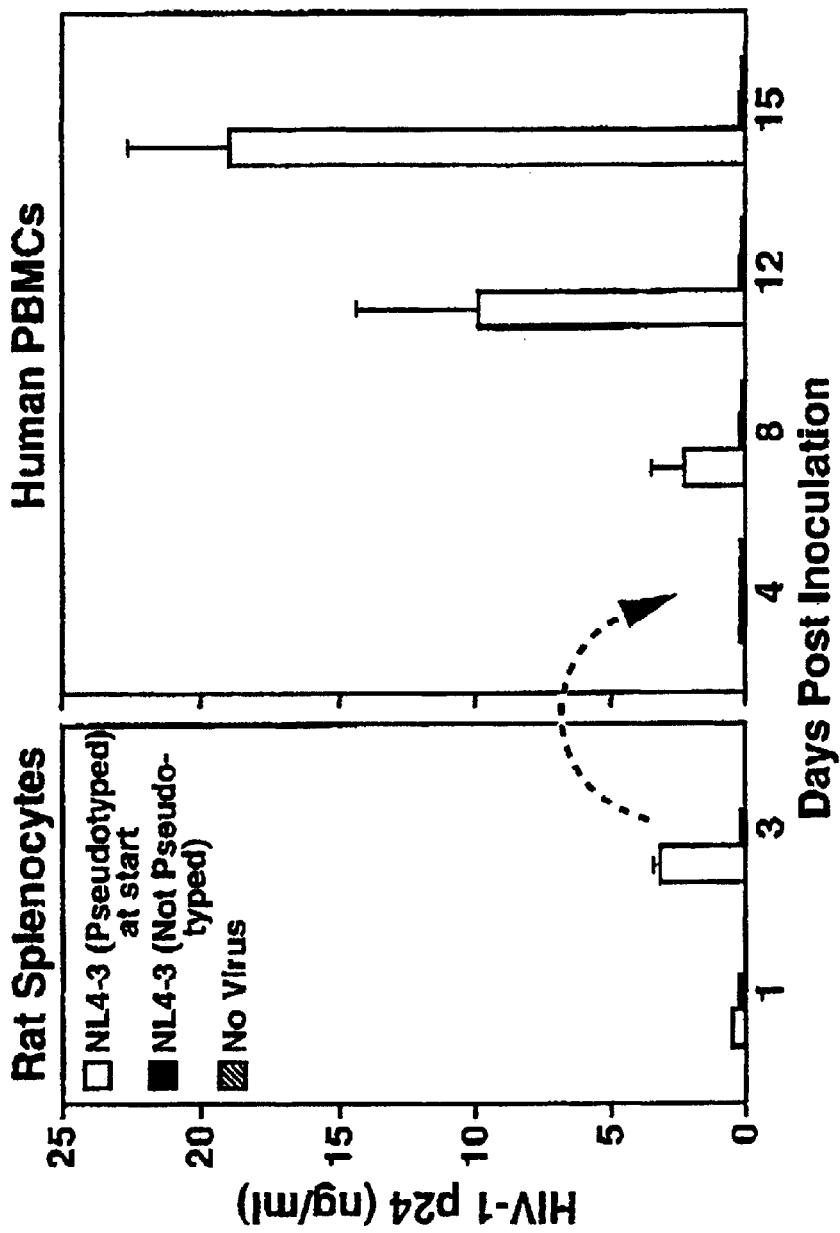
FIG. 1 is a bar graph illustrating the ability of rat splenocytes to produce infectious HIV-1. An open square denotes cells infected with HIV-1 NL4-3 psuedotyped with vesicular stomatitis virus (VSV) G protein, a filled square denotes cells infected with HIV-1 NL4-3 envelope, and hatched square denotes mock infected cells.

Before the present transgenic animals and uses therefor are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a construct" includes a plurality of such constructs and reference to "the chemokine receptor-encoding nucleic acid" and "the CD4-encoding nucleic acid" includes reference to one or more chemokine receptor-encoding nucleic acids and to one or more CD4-encoding nucleic acids, respectively, and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention. Further, the dates of publication provided may be different from the actual publication dates which may need to be independently confirmed.

Definitions

The term "transgene" is used herein to describe genetic material which has been or is about to be artificially inserted into the genome of a non-human mammal, an particularly into a cell of a living non-human mammal.

By "HIV" is meant any virus classified as a primate immunodeficiency virus, which upon infection into a primate and or human causes the immunodisorder AIDS. This includes known strains of HIV, e.g. HIV-1 and HIV-2, variants of these strains, either identified or as yet unidentified, as well as Simian Immunodeficiency Viruses (SIV), variants of SIV and any recombinant chimeras among these strains. This term is also intended to encompass strains of human and primate immunodeficiency virus that are as yet unidentified. This term includes laboratory strains of HIV, recombinant strains of HIV, and primary clinical isolates. Such isolates may be produced using in vitro molecular cloning technology and/or may be isolated from biological samples.

By "HIV associated phenomenon" is meant any combination of physiological, cellular, molecular, or functional event associated with HIV infection. Such phenomenon, include, but are not limited to, viral adhesion to cells, viral integration, viral replication, T-cell depletion, associated opportunistic infections, cancerous alterations, and the like.

By "susceptible to infection" is used to describe a transgenic rodent whose cells are permissible to entry by HIV virus or a transgenic rodent cell permissible to entry by the HIV, and preferably to rodent cells which allow replication of HIV after entry.

By "transformation" is meant a permanent or transient genetic change, preferably a permanent genetic change, induced in a cell following the incorporation of new DNA (i.e. DNA exogenous to the cell). Where the cell is a mammalian cell, a permanent genetic change is generally achieved by introduction of the DNA into the genome of the cell.

By "transgenic rodent" is meant a rodent (e.g., mouse, rat, hamster, etc.), having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

By "bigenic" animal is meant a transgenic animal having at least two transgenes, preferably a first transgene encoding a human CD4 receptor and a second transgene encoding a human chemokine receptor.

By "polygenic" animal is meant an animal having transgenes encoding at least three exogenous genes. In one embodiment, polygenic animals of the invention encode a human CD4 receptor and more than one human chemokine receptor. In another embodiment, polygenic animals of the invention have transgenes encoding a human CD4 receptor, at least one human chemokine receptor, and a protein that interacts with an HIV domain such as a transactivation domain, e.g. Cyclin T.

A "knock-out" of a gene means an alteration in the sequence of the gene that results in a decrease of function of the target gene, preferably such that target gene expression is undetectable or insignificant. A knock-out of an endogenous gene means that function of the gene has been substantially decreased so that expression is not detectable or only present at insignificant levels. "Knock-out" transgenics can be transgenic animals having a heterozygous knock-out of a gene or a homozygous knock-out of a gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic)) of the target gene, e.g., by introduction of an additional copy of the target gene, or by operatively inserting a regulatory sequence that provides for enhanced expression of an endogenous copy of the target gene. "Knock-in" transgenics of interest for the present invention can be transgenic animals having a knock-in of the animal's endogenous CD4 receptor, the animals' endogenous chemokine receptors, or both. Such transgenics can be heterozygous knock-in for the CD4 gene, homozygous for the knock-in of the CD4 gene, heterozygous for the knock-in of a chemokine receptor gene, homozygous for the knock-in of the chemokine receptor gene, or any combination of CD 4 homozygous/heterozygous and chemokine receptor homozygous/heterozygous. "Knock-ins" also encompass conditional knock-ins.

The term "ES cell" as used herein refers to pluripotent embryonic stem cells and to such pluripotent cells in the very early stages of embryonic development, including but not limited to cells in the blastocyst stage of development.

By "construct" is meant a recombinant nucleic acid, generally recombinant DNA, that has been generated for the purpose of the expression of a specific nucleotide sequence (s), or is to be used in the construction of other recombinant nucleotide sequences.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by a CD4 or chemokine receptor sequence).

The term "corresponds to" is meant homologous to or substantially equivalent to or functionally equivalent to the designated sequence.

By "chemokine receptor" is meant a protein that can selectively bind chemokines or other small ligands and affect cellular infection by HIV.

By "binding to an HIV sequence" and the like is meant binding to HIV mRNA, reverse transcribed DNA or any HIV proteins.

By "cDNA" is meant all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein.

By "genomic sequence" is meant a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

Overview of the Invention

The present invention provides transgenic rodent models for HIV infection and phenomenon associated with HIV infection, wherein the transgenic rodent or rodent cell has incorporated into its genome a human CD4 receptor and/or at least one human chemokine receptor. In a preferred embodiment, animals are genetically altered to 1) express a human CD4 and 2) express one or more human chemokine receptors. The transgenic animals may be either homozygous or heterozygous for these genetic alterations. The subject animals are useful for testing candidate agents for treatment of individuals infected with HIV, prior to infection (i.e., a vaccine), prophylactically directly after infection, or after the onset of HIV-related disorders.

Since various rodents studied to date appear to manifest restrictions to viral infection and replication, less restricted rodent species were examined that might be better for transgenic manipulation. In particular, rat cells were examined for several reasons, including: (1) rats are convenient to breed; (2) the immune system of the rat is relatively well characterized and numerous reagents are available for long-term studies; and (3) transgenesis has been performed successfully with rats.

The present invention is based on the discovery that rat cells are susceptible to infection with HIV, as well as capable of expression of the structural genes of HIV. Therefore, the transgenic rodents of this invention are characterized by being susceptible to infection with HIV, and capable of expression of the structural genes of HIV. The transgenic rodents of this invention are preferably further characterized by allowing for HIV replication within the cells of the transgenic rodent. The transgenic rodent or transgenic rodent cells of this invention are useful for a variety of applications, including, but not limited to, studies on HIV infection, HIV replication, and HIV pathogenicity, and screening of candidate agents for antiviral and/or vaccine strategies.

Bigenic animals of the invention overcome the infectivity problem seen with rodents that are singly transgenic for human CD4. In addition, viral infection and replication may be enhanced through the introduction of additional human genes encoding proteins that interact with viral sequences, such as human Cyclin T.

Although the transgenic rodents are described herein as being useful for the study of HIV infection and identification of candidate agents for treatment and/or prevention of HIV infection, the transgenic rodents are also envisioned as being useful in the study of any virus or microbial pathogen that utilizes the human CD4 and/or chemokine receptors. Thus, the descriptions relating to use of the transgenic rodents in the study of HIV, assays of HIV infection, and identification of candidate agents for the prevention and/or treatment of HIV infection are applicable to infection by other virus and microbial pathogens as will be apparent to one skilled in the art upon reading the present disclosure.

Transgenic Animals

A transgene having a gene of interest (e.g. CD4 or a chemokine receptor) is used to transform a cell, meaning that a permanent or transient genetic change, preferably a permanent genetic change, is induced in a cell following incorporation of the exogenous DNA of the transgene. A permanent genetic change is generally achieved by introduction of the DNA into the genome of the cell. Vectors for stable integration include plasmids, retroviruses and other animal viruses, YACs, and the like. Of interest are transgenic non-human mammals, e.g. cows, pigs, goats, horses, etc., and particularly rodents, e.g. rats, mice, hamsters, etc. Preferably, the transgenic animals are rats.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The exogenous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

In general, the transgenic rodents of the invention comprise genetic alterations to provide for 1) expression of human CD4 and 2) expression of at least one human chemokine receptor, e.g. CCR5. Specific CD4- and chemokine receptor-encoding constructs of interest are described below.

The transgenic animals of the invention can comprise other genetic alterations in addition to the presence of the CD4-encoding sequence or the chemokine receptor-encoding sequences. For example, the host's genome may be altered to affect the function of endogenous genes (e.g., endogenous CD4 and/or chemokine receptor genes), contain marker genes, or other genetic alterations consistent with the goals of the present invention.

Knockouts and Knockins

Although not necessary to the operability of the invention, the transgenic animals described herein may comprise alterations to endogenous genes in addition to the genetic alterations described above. For example, the host animals may be either "knockouts" and/or "knockins" for a target gene(s) as is consistent with the goals of the invention (e.g, the host animal's endogenous CD4 may be "knocked out" and/or an endogenous chemokine receptor gene "knocked in"). Knockouts have a partial or complete loss of function in one or both alleles of an endogenous gene of interest (e.g. CD4). Knockins have an introduced transgene with altered genetic sequence and/or function from the endogenous gene. The two may be combined, for example, such that the naturally occurring gene is disabled, and an altered form introduced. For example, it may be desirable to knockout the host animal's endogenous CD4 gene, while introducing an exogenous CD4 gene (e.g. a human CD4 gene).

In a knockout, preferably the target gene expression is undetectable or insignificant. For example, a knock-out of an CD4 gene means that function of the CD4 has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the "knock-out". A chromosomal deletion of all or part of the native gene may be induced, including deletions of the non-coding regions, particularly the promoter region, 3' regulatory sequences, enhancers, or deletions of gene that activate expression of CD4. A functional knock-out may also be achieved by the introduction of an anti-sense construct that blocks expression of the native genes (for example, see Li and Cohen (1996) *Cell* 85:319–329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

It should be noted that while a host CD4 and/or chemokine receptor gene can be knocked out in the transgenic animals of the invention, it is not necessary to the utility of the bigenic human CD4/ chemokine receptor animal.

A "knockin" of a target gene means an alteration in a host cell genome that results in altered expression or function of a native target gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or represser. The use of knockin technology may be combined with production of exogenous sequences to produce the transgenic animals of the invention. For example, the CD4/ chemokine receptor transgenic animals of the invention may contain a knockin of the host's endogenous CD4-encoding sequences to provide for the desired level of CD4 expression in T cells, and contain an exogenous human chemokine receptor-encoding sequence.

Nucleic Acid Compositions

Constructs for use in the present invention include any construct suitable for use in the generation of transgenic animals having the desired levels of expression of a desired CD4-encoding sequence and selected chemokine receptor. These constructs may contain cDNA, genomic sequences, or both. Methods for isolating and cloning a desired sequence, as well as suitable constructs for expression of a selected sequence in a host animal, are well known in the art. The construct can include sequences other than the CD4- and chemokine receptor-encoding sequences, and in one preferred embodiment the rodent also expresses at least one HIV sequence encoding an HIV protein. In addition, a marker gene such as lac Z may be included in the construct, where upregulation of expression of the encoded sequence will result in an easily detected change in phenotype.

The terms "CD4 gene" and "chemokine receptor gene" are used generically to mean human CD4 genes and chemokine receptor genes, e.g. isoforms, alternate forms, splice variants, mutated variants, etc. of these human genes. These terms are also intended to mean the open reading frame encoding specific polypeptides, introns, and adjacent 5' and 3' non-coding nucleotide sequences involved in the regulation of expression, up to about 1 kb beyond the coding region, but possibly further in either direction. The DNA sequences encoding CD4 and/or a chemokine receptor may be cDNA or genomic DNA or a fragment thereof. The genes may be introduced into an appropriate vector for extrachromosomal maintenance or for integration into the host.

The genomic sequences of particular interest comprise the nucleic acid present between the initiation codon and the stop codon, including all of the introns that are normally present in a native chromosome. They may further include the 3' and 5' untranslated regions found in the mature mRNA. They may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kb or smaller; and substantially free of flanking chromosomal sequence.

The sequences of the 5' regions of the CD4 gene, and further 5' upstream sequences and 3' downstream sequences, may be utilized for promoter elements, including enhancer binding sites, that provide for expression in tissues where CD4 is normally expressed. The tissue specific expression is useful for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1:194–205; Mortlock et al. (1996) *Genome Res.* 6:327–33; and Joulin and Richard-Foy (1995) *Eur J Biochem* 232:620–626.

The nucleic acid compositions used in the subject invention may encode all or a part of human CD4 and a chemokine receptor as appropriate. For example, human-rodent chimeras of these genes may be used in place of the full-length human CD4 and/or chemokine receptor gene. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used.

The human CD4 and selected human chemokine receptor may be used separately to generate two (or more) transgenic rodent lines: one transgenic for the human CD4 receptor, and the other transgenic for the selected human chemokine receptor. The two lines can be mated to generate a rodent transgenic for both a human CD4 and a human chemokine receptor. Alternatively, the human CD4 and selected chemokine receptor may be introduced into the same rodent embryo or ES cell, either as part of the same vector or on separate vectors to generate a transgenic rodent carrying both the human CD4 and selected human chemokine receptor.

The nucleic acid sequences for the human CD4 and human chemokine receptor used to produce the transgenic rodent of the subject invention may encode all or a part of the human CD4 receptor or human chemokine receptor as appropriate. Preferably, the coding sequence for CD4 and the selected chemokine receptor include regions sufficient to effect entry of HIV into the cells of the transgenic rodent. By way of example, regions of the coding sequence for CD4 may include the D1-D4 domains in the extracellular region of the protein, and regions of the coding sequence of the selected chemokine receptor may include segments encoding the amino terminus, extracellular binding regions and/or transmembrane domain regions.

Portions or fragments of the coding sequence for human CD4 and the selected chemokine receptor may be obtained by chemically synthesizing oligonucleotides in accordance with conventional methods, by restriction enzyme digestion, by PCR amplification, etc. The introduced coding sequence or parts thereof may be derived from a wild-type genes, naturally occurring polymorphisms, or a genetically manipulated sequences (i.e., deletions, substitutions or insertions in the coding or non-coding regions). Sequences encoding a truncated or altered (e.g, mutated) human CD4 or chemokine receptor are also of interest.

Vectors suitable for use in the present invention comprise at least one expression control element operably linked to the nucleic acid sequence encoding CD4 or a chemokine receptor. Expression control elements are inserted in the vector to control and regulate the expression of the nucleic acid sequence. Examples of expression control elements include, but are not limited to, lac system, operator and promoter regions of phage lamda, yeast promoters, and promoters derived from polyoma, adenovirus, retroviruses, or SV40. The vector may further comprise additional operational elements including, but not limited to, leader sequences, termination codons, polyadenylation signals, and any other sequences necessary or preferred for the appropriate transcription and/or translation of the nucleic acid sequence encoding CD4 or the selected chemokine receptor.

It will be further understood by one skilled in the art that such vectors are constructed using conventional methodology (See e.g. Sambrook et al., (eds.) (1989) "Molecular Cloning, A Laboratory Manual" Cold Spring Harbor Press, Plainview, N.Y.; Ausubel et al., (eds.) (1987) "Current Protocols in Molecular Biology" John Wiley and Sons, New York, N.Y.) or are commercially available.

In some embodiments it may be preferable to express human CD4 and the selected chemokine receptor in tissues that mimic the native pattern of expression in humans. A specific expression pattern may be accomplished by placing the nucleic acid encoding the human CD4 or selected chemokine receptor under the control of an inducible or developmentally regulated promoter, or under the control of a tissue specific or cell type specific promoter (e.g a lymphocyte specific promoter). By way of example, specific expression patterns may be accomplished by the use of genomic sequences for the human CD4 or selected chemokine receptor.

The CD4-encoding construct can contain a wild-type sequence encoding CD4 or mutant forms of CD4, especially those that may alter host specificity of HIV in humans. Likewise, the specific chemokine receptor-encoding construct can contain a wild-type chemokine receptor-encoding sequence or a sequence encoding a modified chemokine receptor. Where desirable, the CD4 and/or chemokine receptor sequences, including flanking promoter regions and coding regions, may be mutated in various ways known in the art to generate targeted changes in the sequence of the encoded protein, splice variant production, etc. The sequence changes may be substitutions, insertions or deletions. Deletions may include large changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of CD4 and different chemokine receptors, or to alter properties of the proteins that affect their function or regulation.

Techniques for in vitro mutagenesis of cloned genes are known. Examples of protocols for scanning mutations may be found in Gustin et al., 1993 Biotechniques 14:22; Barany, 1985 Gene 37:111–23; Colicelli et al., 1985 Mol Gen Genet 199:537–9; and Prentki et al., 1984 Gene 29:303–13. Methods for site specific mutagenesis can be found in Sambrook et al., 1989 Molecular Cloning: A Laboratory Manual, CSH Press, pp. 15.3–15.108; Weiner et al., 1993 Gene 126:35–41; Sayers et al., 1992 Biotechniques 13:592–6; Jones and Winistorfer, 1992 Biotechniques 12:528–30; Barton et al., 1990 Nucleic Acids Res 18:7349–55; Marotti and Tomich, 1989 Gene Anal Tech 6:67–70; and Zhu 1989 Anal Biochem 177:120–4.

The CD4 gene, the various chemokine receptor genes, and exemplary derivatives thereof suitable for use in the production of the transgenic animals of the invention are described below.

The Chemokine Receptors

The chemokine receptor-encoding sequence introduced into the bigenic animals of the invention can be any chemokine receptor known in the art, and may be selected in part by the HIV strain to be studied. Examples of primate chemokine receptors that may be used to generate the subject transgenic rodent, include, but are not limited to, CCR3, CCR5, CCR2B, CXCR4, CCR8, GPRL15, STRL33, APJ, and LTB$_4$. One of ordinary skill in the art will appreciate that the selection of the chemokine receptor to be used in conjunction with the CD4 receptor will depend, in part, on the cellular tropism and chemokine receptor preference of the HIV stain that is to be used to infect the transgenic rodent of the subject invention. For example, if a macrophage-tropic non-synctium-inducing isolate of HIV-1 is to be used, the selected chemokine receptor may be CCR5 (See, e.g. Huang et al. (1996) Nature Medicine 2: 1240–1243). Several chemokine receptor sequences have been isolated, cloned, and sequenced. Table 1 provides a partial list of chemokine receptor sequences that may be suitable for use in the present invention, as well as Genbank accession numbers relating to such sequences.

TABLE 1

Chemokine Receptor Sequences

| Human Chemokine Receptor Sequence | Reference or GenBank Accession No. | Rodent Chemokine Receptor Sequence | Reference or GenBank Accession No. |
|---|---|---|---|
| CCR2 | | rat CCR2 | U77349 |
| | | mouse CCR2 | U51717 |
| CCR3 | AF026535 | Rat CCR3 | AF003954 |
| | U28694 | | Y13400 |
| CCR5 | AF082742 | mouse CCR5 | AF022990 |
| CCR8 | U45983 | | |
| CXCR4 | AF025375 | rat CXCR4 | U90610 |
| | AF052572 | | |
| CCR2B | AF013958 | | |
| GPR15 | U34806 | | |
| STRL33 | U73529 | | |
| | U73530 | | |
| | U73531 | | |
| APJ | H14301 | mouse APJ | U73531 |
| | U03642 | | AA098426 |
| LTB$_4$ | AB002455S | | |

The transgene encoding the human chemokine receptor should preferably provide for expression and secretion of the polypeptide as a bioactive peptide. Expression of chemokine receptor in the host animal can be either constitutive or inducible. Exogenous human chemokine receptor expression may be either systemic or tissue-specific, preferably tissue-specific (e.g., expression of human chemokine receptor substantially specifically in T-cells and/or macrophages).

The chemokine receptor encoding sequence may also be provided as a fusion protein. Methods for production of a chemokine receptor constructs are well known in the art (see, e.g. R. E. Atchison et al., Science 274:1924–6 (1996).

The CD4 Gene and its Derivatives

The nucleic acid sequences encoding the human CD4 receptor or the human chemokine receptor may be cDNA or genomic DNA or a fragment thereof. Sequences for human CD4 are known in the art may also be used with rodent CD4 genes known in the art to create chimeric human/rodent transgenes that allow infectivity of HIV in a rodent model. Table 2 provides a list of human and mouse CD4 sequences useful in the production of the transgenes of the present invention, and provides Genbank accession numbers relating to the listed CD4 sequences.

TABLE 2

Human and Mouse CD4 Sequences

| Human CD4 Sequences | Reference or GenBank Accession No. | Mouse CD4 Sequences | Reference or GenBank Accession No. |
|---|---|---|---|
| Human CD4 gene | X87579 | Mouse T-cell differentiation antigen CD4 gene | SEG_MUSCD4 |
| Human CD4 exon 1, promoter | S68043 | Mouse T-cell differentiation antigen CD4 (L3T4) gene, exons 8–10 | M17080 |
| Human surface glycoprotein variant (CD4) | U40625 | Mouse T-cell differentiation antigen CD4 (L3T4) gene, exon 7 | M17079 |
| | | Mouse T-cell differentiation antigen CD4 (L3T4) gene, | M17078 |

TABLE 2-continued

Human and Mouse CD4 Sequences

| Human CD4 Sequences | Reference or GenBank Accession No. | Mouse CD4 Sequences | Reference or GenBank Accession No. |
|---|---|---|---|
| | | exon 6, and brain allele, exon 1 | |
| | | Mouse T-cell antigen CD4 (L3T4) gene, exons 4 and 5 | M17077 |
| | | Mouse T-cell differentiation antigen CD4 (L3T4) gene, exons 2 and 3 | M17076 |
| | | Mouse T-cell differentiation antigen CD4 (L3T4) gene, exon 1 | M17075 |

Other Human Genes

A number of other human proteins are known to be involved in HIV infectivity, pathogenesis, replication, etc. The bigenic animals of the invention may carry additional human genes that may enhance the ability of HIV to infect the cells, replicate, and the like. In one preferred embodiment, the transgenic rodents of the invention have a stably transmitted human gene encoding a protein involved in HIV transcription and/or viral protein production. For example, a human transcription elongation factor P-TEFb, consisting of a number of subunits including CDK9 kinase, cyclin T and other associated factors, has been shown to interact with Tat to restore Tat activation in HeLa nuclear extract depleted of P-TEFb. Zhou Q, et al. *EMBO J.*, 17:3681–91 (1998). Rodents carrying one or more human subunits may enhance HIV replication in vivo.

Human cyclin T, an 87 kDa cyclin C-related protein, interacts specifically with the transactivation domain of HIV Tat. The interaction of Tat with cyclin T strongly enhances the affinity and specificity of the Tat:TAR RNA interaction, and confers a requirement for sequences in the loop of TAR that are not recognized by Tat alone. Overexpression of human cyclin T has been shown to rescue Tat activity in nonpermissive rodent cells (Wei P, et al., *Cell*, 92:451–62 (1998)). In a preferred embodiment, a human cyclin T gene is stably transmitted to the genome of a bigenic rodent of the invention.

Methods of Making Transgenic Animals

DNA constructs for random integration need not include regions of homology to mediate recombination. Where homologous recombination is desired, the DNA constructs will comprise at least a portion of the target gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or embryonic cells may be obtained freshly from a host, e.g. mouse, rat, hamster, etc. Such cells are grown on an appropriate fibroblast-feeder layer or grown in the presence of appropriate growth factors, such as leukemia inhibiting factor (LIF). When ES cells have been transformed, they may be used to produce transgenic animals.

The means by which the embryonic cell or rodent ES cell may be transformed with the vector comprising the nucleic acid sequences encoding all or part of either the human CD4 or selected chemokine receptor includes, but is not limited to, microinjection, electroporation, transduction, transfection, lipofection calcium phosphate or other procedures known to one skilled in the art. Preferred means includes microinjection and electroporation. For various techniques for transforming mammalian cells, see Keown et al. 1990 *Methods in Enzymology* 185:527–537.

After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

Where bigenic human CD4/ chemokine receptor animals are desired, the rats are preferably generated by crossing a singly transgenic human CD4 animal with a singly transgenic chemokine receptor animal and identifying bigenic animals according to methods well known in the art.

Drug Screening Assays

Through use of the subject transgenic animals or cells derived therefrom, one can identify ligands or substrates that modulate phenomena associated with HIV infection, e.g., viral adhesion to cells, viral integration, viral replication, T-cell depletion, associated opportunistic infections, cancerous alterations, etc. Of particular interest are screening assays for agents that have a low toxicity for human cells.

A wide variety of assays may be used for this purpose, including behavioral studies, determination of the localization of drugs after administration, immunoassays to detect amyloid deposition, and the like. Depending on the particular assay, whole animals may be used, or cells derived therefrom. Cells may be freshly isolated from an animal, or may be immortalized in culture. Cells of particular interest are immune cells.

The term "agent" as used herein describes any molecule, e.g. protein, small molecule, or pharmaceutical, with the capability of preventing or suppressing the molecular and clinical phenomena associated with HIV infection. This includes agents that may prevent, treat and/or ameliorate HIV-associated phenomena, including vaccines). Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening may be directed to known pharmacologically active compounds and chemical analogs thereof.

The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent that approaches an upper limit of the amount that can be delivered successfully to the animal), and may include delivery of the agent in different formulation. The agents can be administered singly or can be combined in combinations of two or more, especially where administration of a combination of agents may result in a synergistic effect. The effect of agent administration upon the transgenic rodent can be monitored by conventional methodology.

The transgenic rodent or rodent cells of the subject invention can also be used to study the infectivity, that is, the permissivity of the cell to entry of HIV. For example, the subject transgenic rodent or rodent cells provides a convenient means of performing comparison studies on wild type and attenuated strains of virus, or among different isolates. After infection of a suitable number of transgenic cells or animals with a selected attenuated strain or isolate, determinations are made as to the effects of infection (e.g. via histology, viability of various cell subsets, response to drugs, viral replication etc.) relative to infection by a representative HIV strain, preferably HIV-1 or HIV-2. The comparative studies are useful for determining how much damage is caused by attenuated strains or new isolates relative to a representative HIV.

Chimeric virus containing selected HIV sequences and other viral sequences are useful as surrogates for HIV in transgenic animals for a broad range of purposes, i.e. essentially for everything that HIV itself might be used. Such a chimera may be especially useful as a surrogate by providing certain desirable characteristics, e.g., by providing higher viral levels in the transgenic rodent.

For instance, infection of the transgenic rodent with a chimeric viral construct may be used to identify regions of HIV that are involved in the infectivity and/or pathogenicity of HIV by infecting the rodents with a chimeric virus containing selected HIV sequences and other, non-HIV viral sequences. By selecting certain HIV sequences and combining these sequences with other viral sequences, the ability of the selected HIV sequences to specifically mediate infection and replication in human cells can be examined. This can provide valuable information for designing therapeutic agents, such as vaccines, as the agents can be designed to target the HIV sequences identified as being important in viral processes.

In another example, the chimeric virus may be a surrogate to determine the predicted effects of an agent on a human subject infected with HIV by administering an agent to a transgenic rodent infected with the chimeric HIV virus. The response of the rodent to the candidate agent can be predictive of the response of the human subject to a therapeutic designed to the HIV sequences of the chimeric virus.

This invention also relates to transgenic rodent cells, wherein the transgenic rodent cell has incorporated into its genome a human CD4 receptor and a human chemokine receptor. The transgenic rodent cells of this invention are characterized by being susceptible to infection with HIV, and capable of expression of the structural genes of HIV. The transgenic rodent cells of the subject invention may be selected from any genus of rodent, preferably a rodent from a genus selected from the group consisting of Mus (e.g. mice), Rattus (e.g. rats), and Mesocricetus (e.g. hamsters). More preferably the rodent cells are rat or mouse cells. The transgenic rodent cells can be generated using the same coding sequences for the human CD4 and human chemokine receptor, the same vectors and the same means of transformation as described above for the generation of transgenic rodent. Examples of rodent cells that may be used include, but are not limited to, rat ES cells, mouse ES-D3 cells (ATCC® No. CRL-1934), mouse ES-E14TG2a cells (ATCC® No. CRL-1821), mouse SCC-PSA1 cells (ATCC® No. CRL-1535), Rat-2 cells (ATCC® No. CRL-1764) and the like.

The transgenic cells of this invention are also useful for a variety of applications, including, but not limited to, studies on HIV infection, HIV replication, and HIV pathogenicity, and screening of candidate agents for antiviral strategies.

The HIV strain used to in HIV, and preferably HIV-1 or HIV-2. Examples of recombinant HIV clones include, but are not limited to, pseudotyped virus (e.g. all or part of the HIV structural genes and the env of another virus, such as vesicular stomatitis virus (VSV)).

Virus stocks used may be titered by conventional methodology including, but not limited to endpoint dilution on human peripheral blood lymphocytes (PBL) See e.g. Weiser B, et al.,PNAS 91:8037–41 (1994). In vitro HIV infectivity, gene expression, and replication can be monitored by a variety of methods known to those skilled in the art. By way of example, such methods may include immunochemical assays (e.g. immunocytochemistry, FACS, Western, ELISA etc.) for p24 to determine gene expression (see, e.g. Atchison, R. E. et al. (1996) *Science* 274:1924–1926); assessment of Rev function by an S1 nuclease assay (Malim, M. et al. (1993) *Mol. Cell. Biol.* 13: 6180–6189); assessment of Tat function by cotransfection of an HIV-1-LTR construct (linked to a reporter gene) with or without a Tat expression vector (Newstein, M. et al. (1990) *J. Virol.* 64:4565–4567); and quantization of infectious virion production by harvesting supernatants and performing reinfection endpoint analysis on representative human cells.

In vivo infections may also be monitored by several methods. By way of example, methods include, but are not limited to, seroconversion can be monitoring of peripheral blood samples using commercially available kits, or PCR analysis of a tissue sample from the inoculated transgenic rodent for the presence of gag p24.

Production of Therapeutic Agents in the Rodents of the Invention

The transgenic rodents of the invention may be used to produce human therapeutic agents (e.g. proteins, peptides, antibodies, and the like). Since the rodents express the human CD4 and/or human chemokine receptors, certain therapeutic agents produced in the transgenic rodents may be suited for use in a human. In one example, a transgenic rodent expressing a human chemokine receptor is inoculated with a target peptide or protein. The resulting antibodies against this peptide or protein will not have an adverse immunological reaction against the human receptor, since the rat antibodies will not recognize the human receptor as foreign. Such antibodies may be useful as vaccines for the prevention and/or amelioration of HIV infectivity and pathogenesis. In another example, a nucleic acid sequence encoding a therapeutic may be introduced to the transgenic rodent. Preferably, such a nucleic acid would be introduced to the rodent in an appropriate expression vector, such as a retroviral or adenoviral vector.

The production of therapeutic agents in the transgenic rodents and benefits of using this technique will be apparent to those skilled in the art upon reading the present disclosure.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Although the present invention has been described in some detail by way of illustration for purposes of clarity of understanding, it will be apparent that certain changes and modifications may be practiced within the scope of the claims. Such modifications and variations which may be apparent to a person skilled in the art are intended to be within the scope of this invention.

Example 1

Restrictions to HIV-1 Replication in Rodent Cells

Rodent cells (CHO) and a radiation hybrid containing human chromosome 12 (known as CHO-12) were challenged with HIV-1 reporter viruses. These replication-defective viruses were pseudotyped with the VSV-G protein to bypass HIV-specific entry requirements, and they contain the firefly luciferase gene to provide a quantitative marker of successful reverse transcription, integration and viral gene expression. In this system, CHO-12 cells displayed a strong luciferase signal upon infection by the reporter virus, while parental CHO cells exhibited a markedly (100-fold) reduced signal. This result is consistent with the known impairment of Tat-dependent transcription function in parental CHO cells. The molecular basis of this restriction within the viral life cycle was investigated by transfecting an expression plasmid encoding human cyclin T into both target cells and inoculating the cultures with the reporter virus. Indeed, cyclin T significantly reconstituted the luciferase signal in CHO cells while it had little effect in CHO-12 cells.

To clarify further the various restrictions to HIV-1 replication in CHO cells, CHO and CHO-12 cells were challenged with BaL, a replication-competent, CCR5-dependent strain of HIV-1, and intracellular expression of the structural gene product p24 was quantitated as an indicator of successful progress of all viral steps leading to late gene expression. Neither CHO nor CHO-12 cells exhibited significant expression of the viral antigen in the absence of complete receptors for HIV-1, suggesting that cellular entry was limiting productive infection despite reconstitution of Tat-dependent function in CHO-12 cells (FIG. 2A). Importantly, CHO-12 but not parental CHO cells displayed significant expression of intracellular p24 upon cotransfection of expression plasmids encoding human CD4 and human CCR5, indicating that successful infection was restored when both the cellular entry and Tat-dependent functions were permitted. Parallel results were obtained upon infection of CHO cells transiently expressing human CD4, human CCR5 and human cyclin T.

Example 2

Permissivity of Rat Cells for HIV infection

Cell lines expressing human CD4 or human CD4 with human CCR5 were derived by transfection of Rat-2 cells and selection with antibiotics. Cell surface expression of the appropriate proteins was verified by flow cytometry. Rat-2-CD4/ CCR5 cells challenged with the replication-competent HIV-1 strain BaL displayed marked cytopathic effects and production of numerous multinucleated structures representing cellular syncytia, whereas uninfected cultures or Rat-2-CD4 cells exhibited no such effects. These findings served as a first indication that Rat-2-CD4/ CCR5 cells are permissive for productive infection by HIV-1. Further evidence was obtained by measuring secreted viral p24 in the supernatants of cultures of Rat-2, Rat-2-CD4 or Rat-2-CD4/CCR5 cells inoculated with BaL; Rat-2 -CD4/ CCR5 cells, but not the others, yielded significant p24 levels in the supernatants. Furthermore, time course studies were performed by pulsing the cultures with BaL overnight, extensively washing the cells with fresh medium the next day, and monitoring extracellular p24 levels in the supernatants at subsequent time points. These experiments showed a progressive increase of p24 levels in the medium, which provides further substantiation of productive infection of these cells. Additionally, supernatants from inoculated Rat-2-CD4/ CCR5 cells, but not of Rat-2-CD4 cells, contained replication-competent virus as demonstrated upon transfer to cultures of activated human peripheral blood mononuclear cell.

To assess the permissivity of rat lymphocytes for HIV-1 gene expression, reporter (luciferase) viruses pseudotyped with either VSV-G or amphotropic Moloney murine leukemia virus envelope proteins were used to challenge the rat T-cell line NB-2. Both pseudotype stocks yielded luciferase signals in NB-2 cells that exceeded those produced in the human T-cell line Jurkat. Therefore, these rat lymphocytes support robust LTR-driven gene expression even in the absence of human cofactors for Tat or other HIV-1 gene products.

Collectively these findings reveal that cells derived from rats are restricted for HIV-1 replication largely at the level of entry due to an absence of the human viral receptor complex, while cells derived from hamsters manifest a selective Tat-dependent restriction in addition to its block to entry. As determined in rat fibroblasts and T lymphocytes, post-entry steps in the viral replication cycle appear to be largely preserved in this species. In particular, Tat and other viral factors such as Rev evidently function at sufficient levels in this host to support replication and production of infectious virions that are competent to spread further. Therefore, reconstitution of a viral receptor complex consisting of human CD4 and a coreceptor such as human CCR5 confers on such cells permissivity to the HIV-1 replication cycle.

Example 3

Production of Infectious HIV-1 in Rat Splenocytes

Purified primary rat splenocytes from outbred Sprague-Dawley rats were activated with plate-immobilized anti-rat CD3 and anti-rat CD28 monoclonal antibodies and human recombinant IL-2 for 2 days. Subsequently, cells were 1) infected with HIV-1 NL4-3, which had been pseudotyped with the vesicular stomatitis virus (VSV) G protein, 2) infected with HIV-1 NL4-3 envelope sequences, or 3) mock infected. See FIG. 1. Viral stocks had been produced by cotransfecting the human 293T cell line with proviral DNA of HIV-1 NL4-3 with either an expression plasmid encoding the VSV-G protein (pseudotyped NL4-3) or an empty expression vector (NL4-3 wildtype). After overnight infection, cells were washed three times with PBS, incubated in trypsin/EDTA for 5 min at 37° C., and washed three times with culture medium. Subsequently, a supernatant aliquot was removed on day 1, and the supernatent analyzed for HIV-1 production by p24 analysis. Another supernatant aliquot was removed on day 3 prior to transfer of supernatants onto activated human peripheral blood mononuclear cells (PBMC). Human PBMC were washed the following day (day 4) and the kinetics of HIV-1 infection in these cultures was monitored by determination of HIV-1 p24 values on days 8, 12, and 15. The rise in p24 values following inoculation of human PBMC indicates that virions derived from the primary rat cells are infectious for human cells.

Example 4

Production of Transgenic Rat Lines

Figure 4:
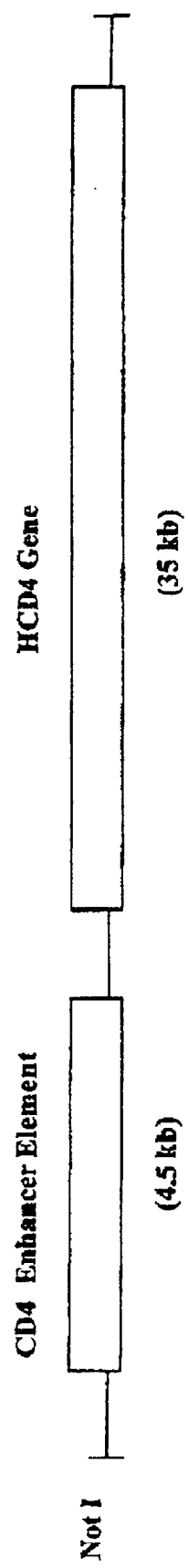
Figure 5:
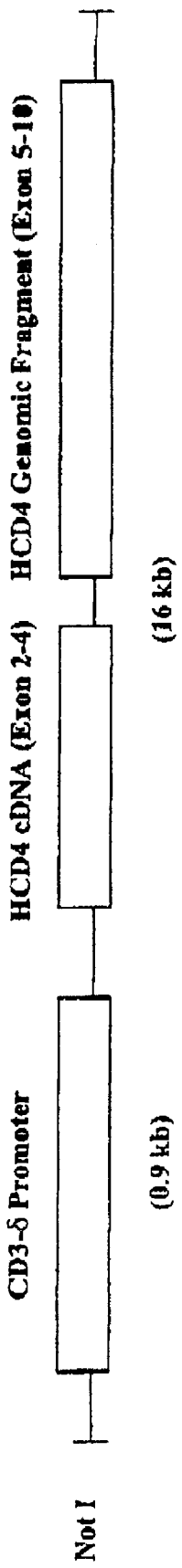

Four transgenic vectors used to prepare rat lines carrying human CD4, CCR5 and CXCR4 are illustrated schematically in FIGS. 2–5. FIG. 2 illustrates a schematic figure of vector pCD4-hCXCR4, which contains a CD4 enhancer/promoter element, the human CD4 intron I, and the human CXCR4 gene. Transgenic rats containing this construct were prepared for this project under contract by Dr. John Mullins (University of Edinburgh). FIG. 3 illustrates a schematic figure of vector pCD4-hCCR5, which contains a CD4 enhancer/promoter element, the human CD4 intron I, and the human CCR5 cDNA. Transgenic rats containing this construct were prepared for this project under contract by a commercial vendor (Chrysalis DNX Transgenic Sciences, Princeton, N.J.), FIG. 4 is a schematic of vector pCD4-hCD4 (Killeen et al., EMBO J. 12:1547–1553 (1993)). Transgenic rats containing this construct were prepared for this project under contract by a commercial vendor. (Chrysalis DNX Transgenic Sciences, Princeton, N.J.). FIG. 5 is a schematic illustrating vector pCD3-hCD4, which contains a CD3 delta-promoter. The transgene consists of a cDNA fragment encoding exons 2–4 and part of exon 5 of the human CD4 gene, fused to a genomic fragment encoding the remainder of exon 5, exons 6–9, and part of exon 10 of the human CD4 gene (Fugger et al., Proc. Natl. Acad. Sci. USA, 91:6151–6155 (1994). The transgenic rat line was produced previously by Drs. Robert Hammer and Joel Taurog (University of Texas, Southwestern).

Example 5

Expression of Human CCR5 Receptor on Lymphocytes of Transgenic Rats

Figure 6:
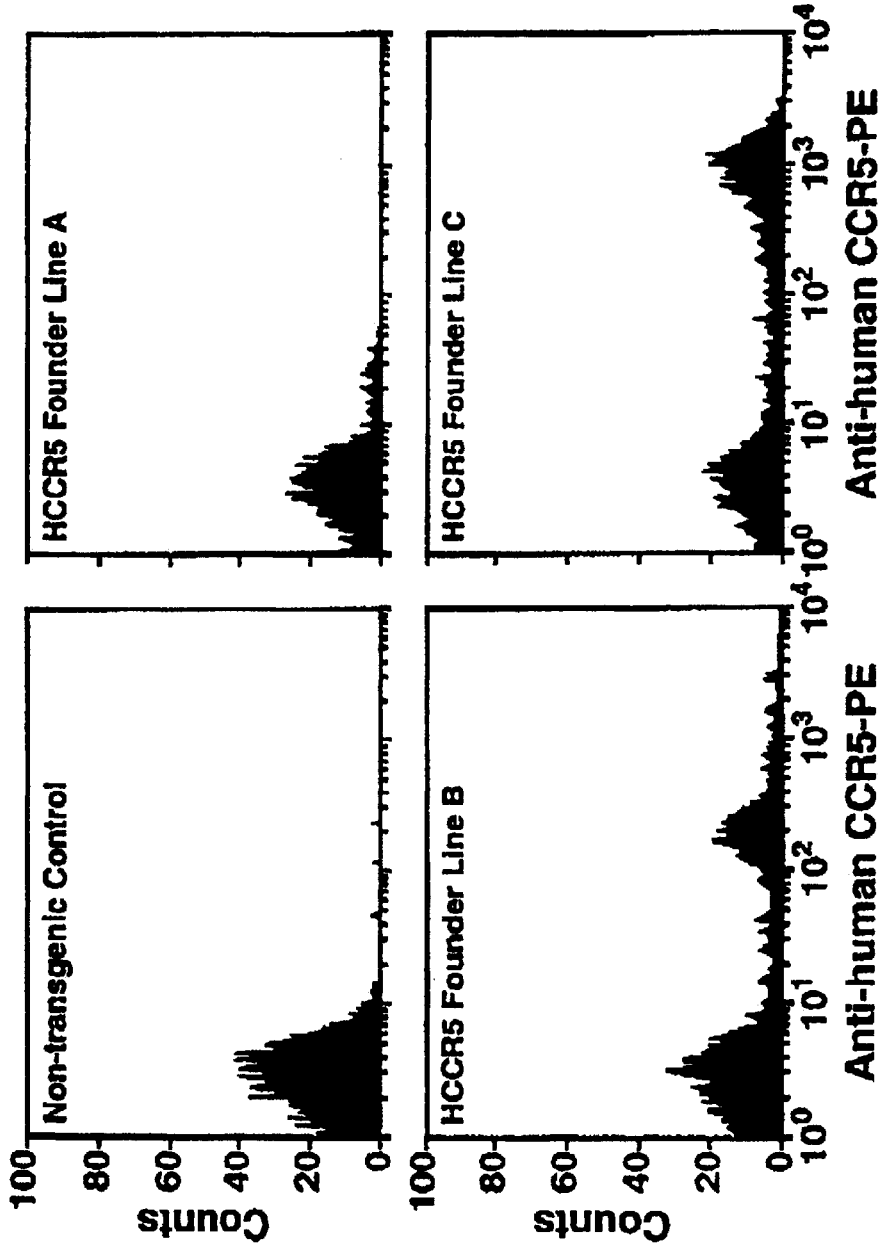
FIG. 6 is a series of four FACScan graphs illustrating expression of human CCR5 on peripheral lymphocytes from human CCR5 transgenic rat lines.

Heparinized blood from rats of the F2 generation of three founder lines (A, B, and C) carrying a human CCR5 transgene and of a non-transgenic control rat was stained with a commercially available PE-conjugated anti-human CCR5 monoclonal antibody and analyzed by FACScan analysis. A significant subset of peripheral lymphocytes in founder lines A, B, C exhibited low, intermediate, or high levels of human CCR5 expression, respectively (See FIG. 6).

Figure 7:
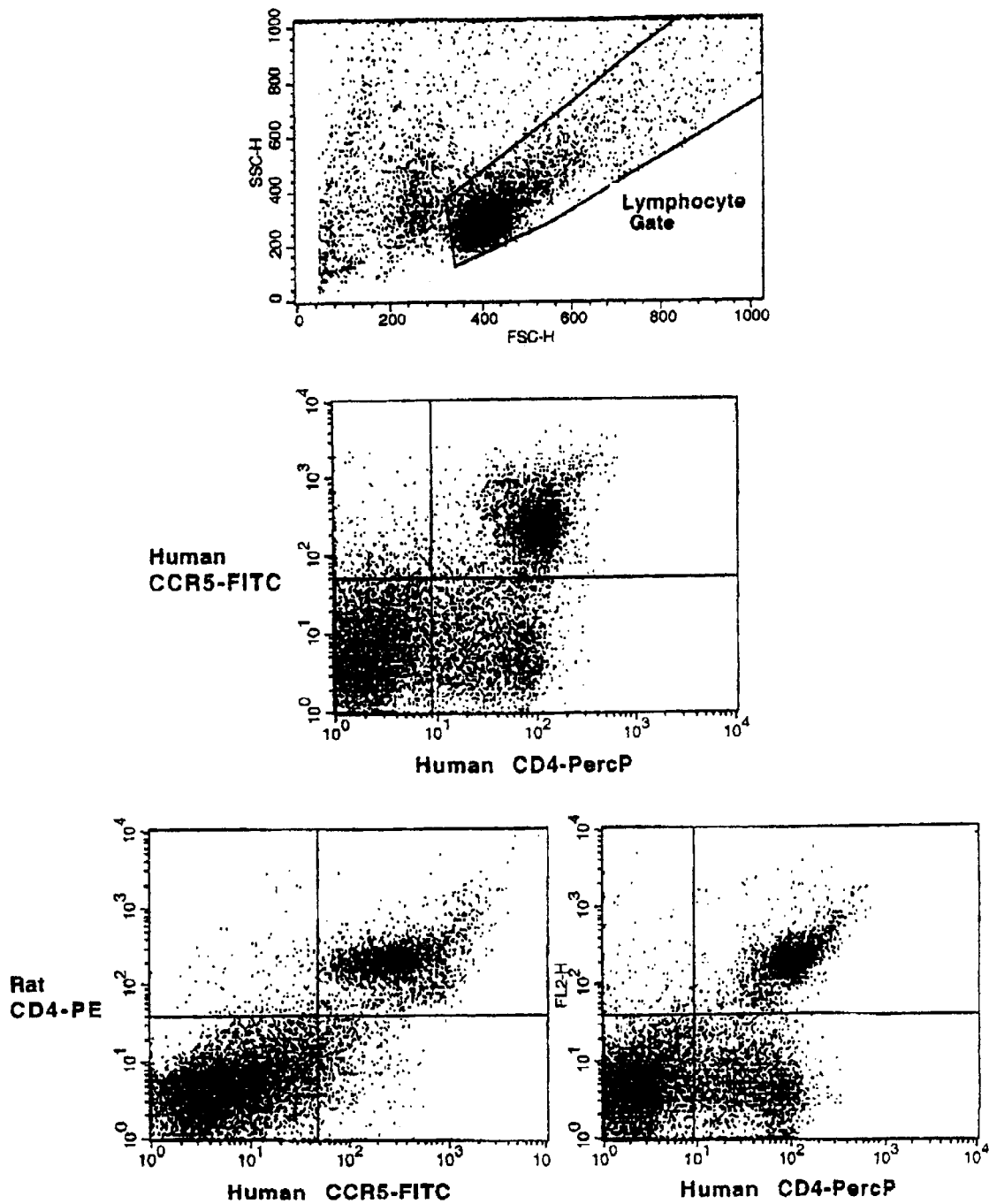
FIG. 7 is a series of four FACScan graphs illustrating coexpression of human CD4 and human CCR5 on CD4-positive T cells derived from double transgenic rats.

Double transgenic CD4/CCR5 rats were produced by mating transgenic animals from each line and selecting for bigenic animals expressing receptors from both transgenes. Specifically, rats were produced from a cross between the human CD4-transgenic line (CD3 promotor-driven expression of CD4) and human CCR5-transgenic line C. Human CD4 and CCR5 antigens were coexpressed on CD4-positive T-cells derived from double-transgenic rats. (See FIG. 7). Splenocytes from a double-transgenic rat were co-stained with a PE-conjugated anti-rat CD4 monoclonal antibody, FITC-conjugated anti-human CCR5 monoclonal antibody, and a PercP-conjugated anti-human CD4 monoclonal antibody and analyzed by FACScan. Cells in the upper right quadrant of FIG. 7 expressed both human CD4 and human CCR5. The lower left panel shows that all cells that expressed human CCR5 were restricted to the endogenous (rat) CD4-positive T-cells. The lower right panel shows that human CD4 was expressed largely on rat CD4-positive T cells, but also on a fraction of rat CD4-negative lymphocytes.

Example 6

Expression of Human CXCR4 Receptor on Lymphocytes of Transgenic Rats

Southern blotting identified two human CXCR4 transgene-positive rat founders. DNA extracted from tail biopsies of seven $G_0$ rats was Sal I/Bgl II-digested and then separated by SDS-PAGE, blotted onto a nylon membrane, and hybridized with a $^{32}P$-labelled human CXCR4 cDNA probe. Autoradiography was carried out at −80° C. for 3 days. A band at 2.7 kb was diagnostic for identifying transgene-integration-positive founders, which had been prepared with a CXCR4 transgene.

Figure 8:
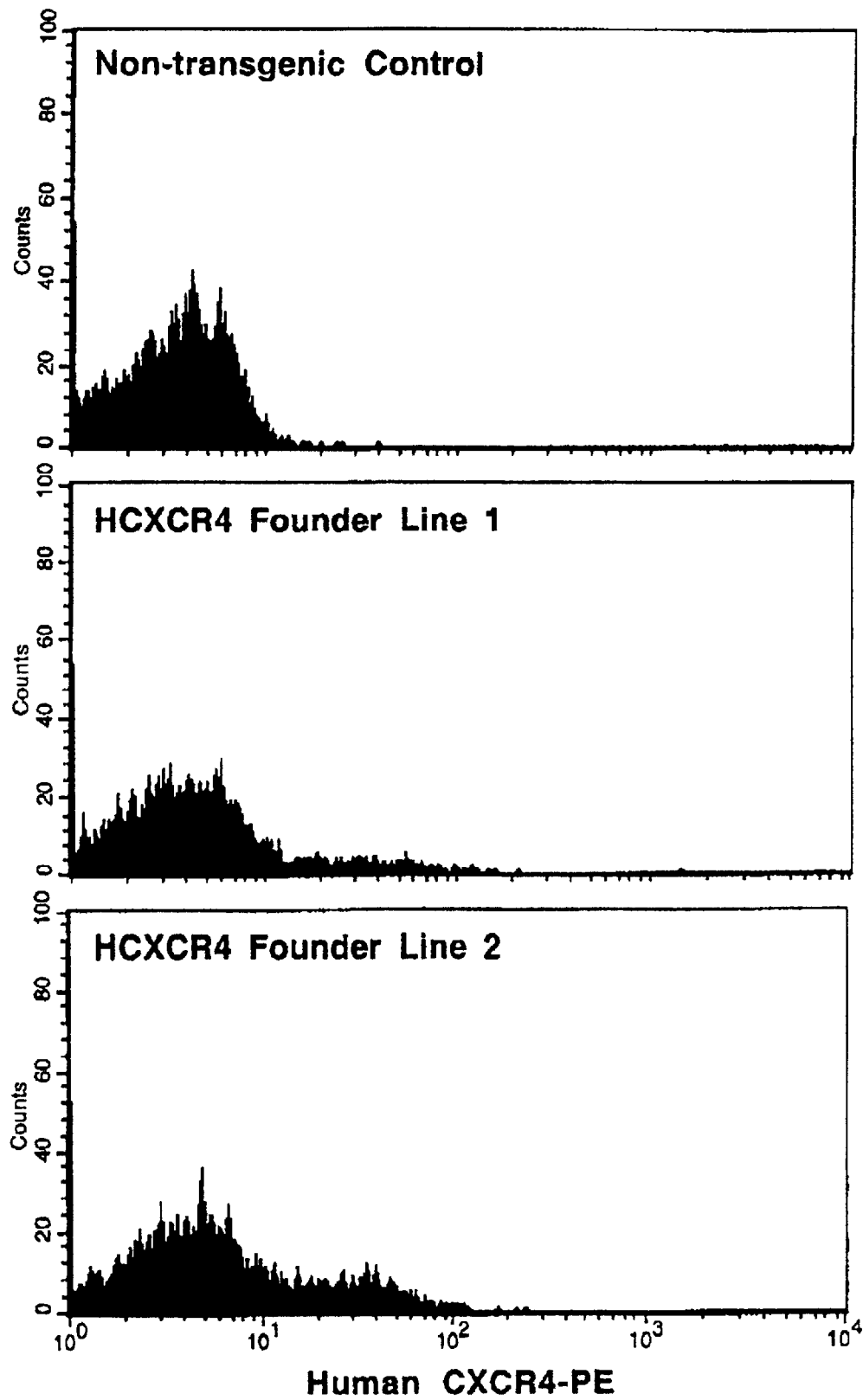
FIG. 8 is a series of three FACScan graphs illustrating expression of human CXCR4 on peripheral lymphocytes from transgenic rat lines.

Human CXCR4 was expressed on peripheral lymphocytes from transgenic rat lines. Heparinized blood from HCXCR4-transgenic founder #54 (founder line 1) and #55 (founder line 2) and from a non-transgenic control rat was stained with a commercially available PE-conjugated monoclonal antibody detecting CXCR4 and analyzed by FACScan. A significant subset of peripheral lymphocytes in founder lines 1 and 2 exhibit intermediate levels of expression of human CXCR4. (See FIG. 8).

Example 7

HIV-1 Infection in Cells Coexpressing Human CD4 and CCR5

Splenocytes from transgenic rats coexpressing human CD4 and CCR5 were shown to be susceptible to infection by HIV-1 strains. Rat splenocytes from a human CD4/CCR5 (line C) double-transgenic rat and a littermate rat that was transgenic solely for human CD4 were cultivated as single cell suspension for two days in medium containing human recombinant IL-2. Subsequently, cells were infected with pseudotyped HIV-1 luciferase reporter viruses containing either the CCR5-specific envelopes of HIV-1 ADA or HIV-1 JRFL, or the CXCR4-specific envelope of HIV-1 NL4–3 (negative control). Pseudotype HIV-1 luciferase reporter viruses had been produced on 293T cells as previously described (Chan et al., J. Virol. 73:2350–2358 (1999)).

Figure 9:
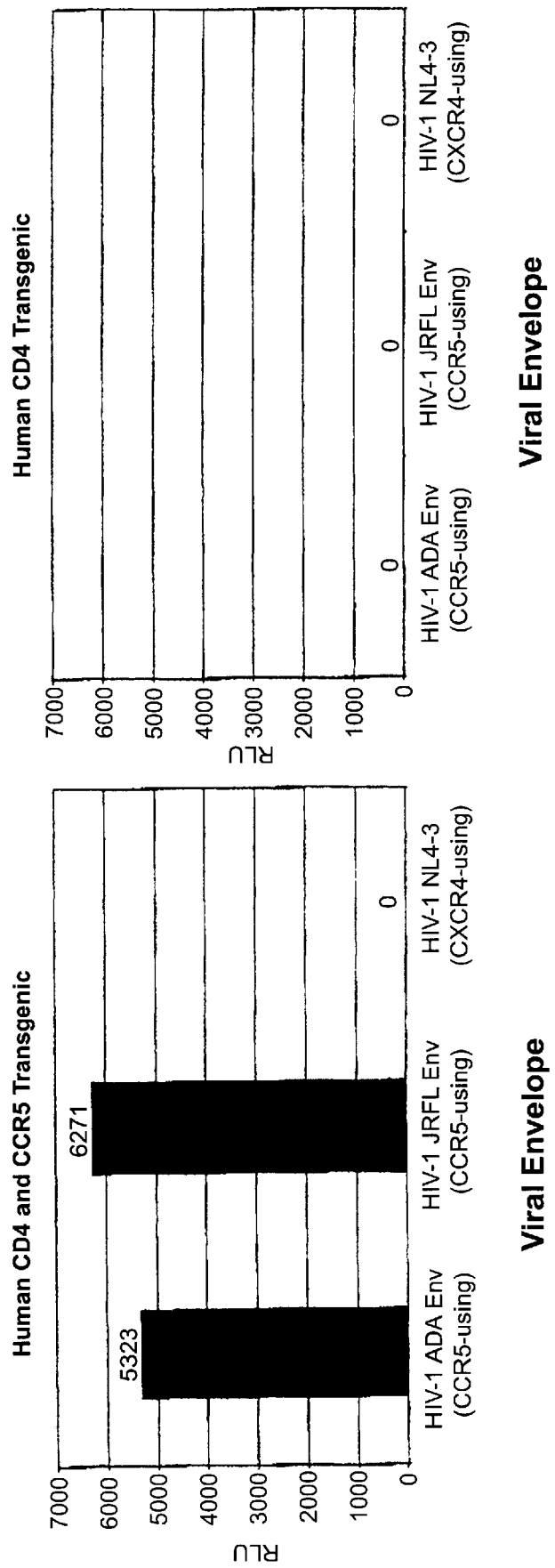
FIG. 9 is a set of two bar graphs showing infection of double transgenic rat splenocytes with a pseudotyped HIV-1 luciferase reporter virus.

Three days post-infection, cells were lysed and assayed for luciferase activity. Values are expressed as Relative Light Units (RLU). Only splenocytes from the double-transgenic rat yielded detectable luciferase activity for both CCR5-using pseudotyped viruses. See FIG. 9. The CXCR4-using HIV-1 NL4-3 pseudotypes did not yield a detectable signal in either the double- or single-transgenic rat cells.

These results demonstrate that coexpression of human CD4 and CCR5 rendered primary rat cells from the transgenic animals permissive for infection by CCR5-using HIV-1 isolates.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure. The invention is thus limited only by the following claims.

What is claimed is:

1. A transgenic rat whose genome comprises a first stably integrated transgenic nucleotide sequence encoding a human CD4 and a second stably integrated transgenic nucleotide sequence encoding a human chemokine receptor;

wherein the first and second transgenes are operably linked to a promoter to be preferentially expressed which results in HIV adhesion and infection of T-cells and/or macrophages.

2. The transgenic rat of claim 1, wherein the chemokine receptor is selected from the group consisting of: CCR3, CCR5, CCR2B, CXCR4, CXR3, CCR8, GPR15, STRL33, APJ, and $LTB_4$.

3. An isolated cell derived from the rat of claim 1, wherein said isolated cell expresses said transgenes.

4. A method for screening for biologically active agents that modulate HIV adhesion and/or infection, the method comprising:

combining a candidate agent with a transgenic rat having a genome comprising an exogenous and stably transmitted transgene encoding a human CD4 and an exogenous and stably transmitted transgene encoding a human chemokine receptor, wherein the first and second transgenes are operably linked to a promoter to be preferentially expressed in T-cells and/or macrophages which results in HIV adhesion and/or infection of cells expressing said transgenes in said transgenic rat; and determining the effect of said agent on HIV infection of said transgenic rat.

5. The method of claim 4, wherein HIV infection is determined by measuring at least one associate HIV phenomena selected form the group consisting of: viral adhesion to cells, viral integration, viral replication and T-cells depletion.

6. A method of screening for biologically active agents that modulate HIV adhesion and/or infection, the method comprising:

combining a candidate agent with a transgenic rat cell culture, each cell of said culture comprising an exogenous and stably transmitted transgene encoding a human CD4 and an exogenous and stably transmitted transgene encoding a human chemokine receptor, wherein the first and second transgenes are operably linked to a promoter to be preferentially expressed in T-cells and/or macrophages; and determining the effect of said agent on HIV infection of said rat cell culture.

7. A method of assessing the infectivity of an HIV isolate comprising:

inoculating a first transgenic rat with an HIV isolate;

inoculating a second transgenic rat with a representative HIV isolate, wherein both transgenic rats have a genome comprising an exogenous and stably transmitted transgene encoding a human CD4 and an exogenous and stably transmitted transgene encoding a human chemokine receptor, wherein the first and second transgenes are operably linked to a promoter to be preferentially expressed in T-cells and/or macrophages such that cells expressing said transgenes are infected by HIV; and comparing the HIV isolate infectivity of the first transgenic rat to the representative HIV infectivity of the second transgenic rat.

8. The method of claim 7, wherein the HIV isolate is a strain of HIV-1.

9. A method for testing the activity of selected HIV sequences, comprising:

providing a transgenic rat having a genome comprising an exogenous and stably transmitted transgene encoding a human CD4 and an exogenous and stably transmitted transgene encoding a human chemokine receptor, wherein the first and second transgene are operably linked to a promoter to be preferentially expressed in T-cells and/or macrophages such that cells expressing said transgenes can be infected by HIV;

infecting the rat with a virus, said virus comprising selected HIV sequences and sequences from a non-HIV virus; and determining the effect of the selected HIV sequences on infection of the transgenic rat by said virus.

10. The method of claim 9, further comprising:

administering to the infected transgenic rat a candidate agent; and determining the effect of the candidate agent on HIV adhesion and/or infection of the infected transgenic rat.

11. A transgenic rat whose genome comprises a first stably integrated transgenic nucleotide sequence encoding a human CD4 and a second stably integrated transgenic nucleotide sequence encoding a human CCR5 chemokine receptor;

wherein the first and second transgenes are operably linked to a promoter to be preferentially expressed in T-cells and/or macrophages which results in HIV adhesion and/or infection of cells expressing said transgenes of said rat.

12. A transgenic rat whose genome comprises a first stably integrated transgenic nucleotide sequence encoding a human CD4 and a second stably integrated transgenic nucleotide sequence encoding a human CXCR4 chemokine receptor;

wherein the first and second transgenes are operably linked to a promoter to be preferentially expressed in T-cells and/or macrophages which results in HIV adhesion and/or infection of cells expressing said transgenes of said rat.

13. An isolated rat cell containing a first stably integrated nucleotide sequence encoding a human CD4 receptor and a second stably integrated nucleotide sequence encoding a human CCR5 chemokine receptor, wherein said isolated cell expresses said transgenes.

14. An isolated rat cell containing a first stably integrated nucleotide sequence encoding a human CD4 receptor and a second stably integrated nucleotide sequence encoding a human CXCR4 chemokine receptor, wherein said isolated cell expresses said transgenes.

15. A method for screening for biologically active agents that modulate HIV adhesion and/or infection, the method comprising:

combining a candidate agent with a transgenic rat having a genome comprising an exogenous and stably transmitted transgene encoding a human CD4 and an exogenous and stably transmitted transgene encoding a human CCR5 chemokine receptor, wherein the first and second transgenes are operably linked to a promoter to be preferentially expressed in T-cells and/or macrophages which results in HIV adhesion and/or infection of cells expressing said transgenes of said rat; and determining the effect of said agent on HIV infection of said transgenic rat.

16. The method of claim 15, wherein HIV infection is determined by measuring at least one associated HIV phenomena at least one selected from the group consisting of: viral adhesion to cells, viral integration, viral replication and T-cell depletion.

17. A method of screening for biologically active agents that modulate HIV adhesion and/or infection, the method comprising:

combining a candidate agent with a transgenic rat cell culture, each cell of said culture comprising an exogenous and stably transmitted transgene encoding a human CD4 and an exogenous and stably transmitted transgene encoding a human CCR5 chemokine receptor, wherein the first and second transgenes are operably linked to a promoter to be preferentially expressed in T-cells and/or macrophages; and determining the effect of said agent on HIV infection of said rat cell culture.

18. A method of assessing the infectivity of an HIV isolate comprising:

inoculating a first transgenic rat with an HIV isolate; inoculating a second transgenic rat with a representative HIV isolate, wherein both transgenic rats have a genome comprising an exogenous and stably transmitted transgene encoding a human CD4 and an exogenous and stably transmitted transgene encoding a human CCR5 chemokine receptor, wherein the first and second transgenes are operably linked to a promoter to be preferentially expressed in T-cells and/or macrophages such that cells expressing said transgenes are infected by HIV; and comparing the HIV isolate infectivity of the first transgenic rat to the representative HIV infectivity of the second transgenic rat.

19. The method of claim 18, wherein the HIV isolate is a strain of HIV-1.

20. A method for testing the activity of selected HIV sequences, comprising:

providing a transgenic rat having a genome comprising an exogenous and stably transmitted transgene encoding a human CD4 and an exogenous and stably transmitted transgene encoding a human CCR5 chemokine receptor, wherein the first and second transgenes are operably linked to a promoter to be preferentially expressed in T-cells and/or macrophages such that cells expressing said transgenes can be infected by HIV;

infecting the rat with a virus, said virus comprising selected HIV sequences and sequences from a non-HIV virus; and determining the effect of the selected HIV sequences on infection of the transgenic rat by said virus.

21. The method of claim 20, further comprising:

administering to the infected transgenic rat a candidate agent; and determining the effect of the candidate agent on HIV adhesion and/or infection of the infected transgenic rat.

* * * * *

UNITED STATES PATENT AND TRADEMARK OFFICE
CERTIFICATE OF CORRECTION

| | |
|---|---|
| PATENT NO. | : 6,372,956 B1 |
| APPLICATION NO. | : 09/470817 |
| DATED | : April 16, 2002 |
| INVENTOR(S) | : Mark A. Goldsmith |

It is certified that error appears in the above-identified patent and that said Letters Patent is hereby corrected as shown below:

Please replace the statement of Government Rights beginning on column 1, line 9, with the following revised statement:

GOVERNMENT RIGHTS

--The United States Government has certain rights in this application pursuant to NIH Grant No. R21 AI42654-02.--

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

PATENT NO. : 6,372,956 B1
APPLICATION NO. : 09/470817
DATED : April 16, 2002
INVENTOR(S) : Goldsmith et al.

It is certified that error appears in the above-identified patent and that said Letters Patent is hereby corrected as shown below:

In the Specification

In Column 1, Lines 9-10 (Approx.), delete "The United States Government may have certain rights in this application pursuant to NIH Grant No. R21 AI42654-02." and insert --This invention was made with government support under AI042654 awarded by the National Institutes of Health. The government has certain rights in the invention.-- therefor Signed and Sealed this
Twenty-sixth Day of March, 2024

Katherine Kelly Vidal
*Director of the United States Patent and Trademark Office*